US00PP11326P

United States Patent [19]

Schmulling

[11] Patent Number: Plant 11,326

[45] Date of Patent: Apr. 4, 2000

[54] HELIOTROPE PLANT NAMED 'ATLANTA'

[75] Inventor: Markus Schmulling, Billerbeck-Beerlage, Germany

[73] Assignee: Outeniqua Nursery, Emerald, Australia

[21] Appl. No.: 09/129,432

[22] Filed: Aug. 5, 1998

[51] Int. Cl.[7] ..... A01H 5/00

[52] U.S. Cl. ..... Plt./226

[58] Field of Search ..... Plt./226, 263

[56] References Cited

U.S. PATENT DOCUMENTS

P.P. 559 12/1942 McKean ..... Plt./263

*Primary Examiner*—Howard J. Locker
*Assistant Examiner*—Kent L. Bell
*Attorney, Agent, or Firm*—C. A. Whealy

[57] ABSTRACT

A distinctive cultivar of Heliotrope plant named 'Atlanta', characterized by its mostly upright and outwardly spreading plant habit; freely branching habit; floriferousness; early flowering; and dark blue purple flower color.

2 Drawing Sheets

BACKGROUND OF THE INVENTION

The present invention relates to a new and distinct cultivar of Heliotrope plant, botanically known as *Heliotropium arborescens*, and hereinafter referred to by the cultivar name 'Atlanta'.

The new Heliotrope is a product of a planned breeding program conducted by the Inventor in Billerbeck, Germany. The new Heliotrope originated from a self-pollination made by the Inventor of the commercial *Heliotropium arborescens* cultivar 'Marine' (not patented).

The cultivar Atlanta was discovered and selected by the Inventor as a flowering plant within the progeny of the stated cross in a controlled environment in Billerbeck, Germany.

Compared to plants of the parent cultivar, 'Marine', plants of the new Heliotrope are more compact, are more freely branching, flower about two weeks earlier, and differ in flower color.

Asexual reproduction of the new Heliotrope by cuttings in Billerbeck, Germany, has shown that the unique features of this new Heliotrope are stable and reproduced true to type in successive propagations.

SUMMARY OF THE INVENTION

Plants of the new Heliotrope have not been observed under all possible environmental conditions. The phenotype may vary significantly with variations in environment such as temperature and light and fertility levels, without, however, any variance in genotype.

The following traits have been repeatedly observed and are determined to be the unique characteristics of plants of the new Heliotrope and differentiate plants of the new Heliotrope from other commercial Heliotrope cultivars:

1. Plants of the new Heliotrope are mostly upright and outwardly spreading in plant habit.

2. Plants of the new Heliotrope are very freely branching.

3. Plants of the new Heliotrope are very floriferous and flower earlier than other Heliotrope cultivars known to the Inventor.

4. Flowers of plants of the new Heliotrope are dark blue purple in color.

BRIEF DESCRIPTION OF PHOTOGRAPHS

The accompanying colored photographs illustrate the overall appearance and flower color of the new Heliotrope, showing the colors as true as it is reasonably possible to obtain in colored reproductions of this type.

The photograph on the first sheet comprises a top perspective view of a typical containerized plant of the cultivar Atlanta.

The photograph at the top of the second sheet comprises a close-up view of typical flowers and leaves of a typical containerized plant of the cultivar 'Atlanta'.

The photograph at the bottom of the second sheet comprises a comparison view of typical plants of the cultivars 'Marine' (left) and 'Atlanta' (right) showing the differences in plant habit. Actual flower and foliage colors may differ from flower and foliage colors in the photographs due to light reflectance.

DETAILED BOTANICAL DESCRIPTION

The following observations, measurements and values describe plants grown in Encinitas, Calif. and Keller, Tex., under conditions which approximate commercial practice. The plants were initially grown in a polyethylene-covered greenhouse and then moved to a full sun to partial shade field situation during the summer. In the following description, color references are made to The Royal Horticultural Society Colour Chart except where general terms of ordinary dictionary significance are used.

Bontanical classification: *Heliotropium arborescens* cultivar 'Atlanta'.

Parentage: Self-pollination of *Heliotropium arborescens* cultivar 'Marine', not patented.

Propagation:

*Type.*—By cuttings.

*Time to initiate roots, summer.*—About 14 to 18 days at temperatures of about 18 to 20° C.

*Time to initiate roots, winter.*—About 18 to 21 days at temperatures of about 20 to 22° C.

*Rooting habit.*—Very fine, freely branching, and fibrous.

Plant description:

*Plant form.*—Mostly upright and outwardly spreading perennial subshrub; inverted triangle. Removal of terminal apices enhances development of axillary branching. Flowers abundant.

*Growth habit*.—Lateral shoots upright, then more outwardly spreading as plants develop. Moderately vigorous.

*Plant height*.—About 30 cm.

*Plant width*.—About 40 cm.

*Stem description*.—Lateral branch diameter: About 4 mm. Internode length: About 7 cm. Texture: Very fine pubescence. Color: 146A.

*Foliage description*.—Arrangement: Single leaves, alternate or whorled. Length: About 5.5 cm. Width: About 2 cm. Shape: Lanceolate to oblong. Apex: Acute. Base: Attenuate. Margin: Entire. Texture: Very tough; rough; fine hairs on both leaf surfaces and margin. Color: Young foliage, upper surface: Greener than 147A. Young foliage, lower surface: Greener than 147B. Mature foliage, upper surface: Greener than 147A. Mature foliage, lower surface: Greener than 147B. Venation, upper surface: Same as leaf color. Venation, lower surface: Close to 147C. Petiole: Length: About 3 mm. Diameter: About 2 mm. Color: Whitish green.

Flower description:

*Flowering habit*.—Five-parted fused tubular flowers arranged in terminal compound cymes. Numerous flowers per cyme and numerous cymes per plant; actual numbers of flowers may vary depending upon temperature and light levels. Flowers are held mostly upright and are not persistent.

*Natural flowering season*.—Spring throughout summer.

*Fragrance*.—Present, slightly sweet.

*Flower size*.—Cymes are about 5 cm in diameter; individual flowers are about 7.5 mm in diameter and about 6 mm in height.

*Flower bud*.—Length: About 3 mm. Diameter: About 1 mm. Shape: Tubular. Color: 90A at apex.

*Petals*.—Arrangement: Typically five fused at base, star-shaped and tubular; petals curved downward with prominently recessed midvein. Appearance: Satiny, smooth, iridescent. Length: About 2.5 mm. Width: About 2.5 mm. Apex: Rounded. Margin: Entire. Color: When opening, upper surface: 90A with white, close to 155D, center. When opening, lower surface: 90B. Opened flower, upper surface; 90A with white, close to 155D, center and throat. Opened flower, lower surface: Light purple to white.

*Sepals*.—Shape: Linear, fused at base. Calyx length: About 4 mm. Calyx diameter: About 1.5 mm. Apex: Sharply acute. Margin: Entire. Texture: Pubescent. Color: Greenish red.

*Reproductive organs*.—Stamens: Anther color: Whitish green to purplish brown. Pollen amount: Scarce. Pollen color: Lemon yellow. Pistils: Stigma color: White to light green.

Disease resistance: Resistance to known pathogens of Heliotrope has not been observed.

Seed production: Plants of the new Heliotrope have not been observed to produce seed.

I claim:

1. A new and distinct Heliotrope plant named 'Atlanta', as illustrated and described.

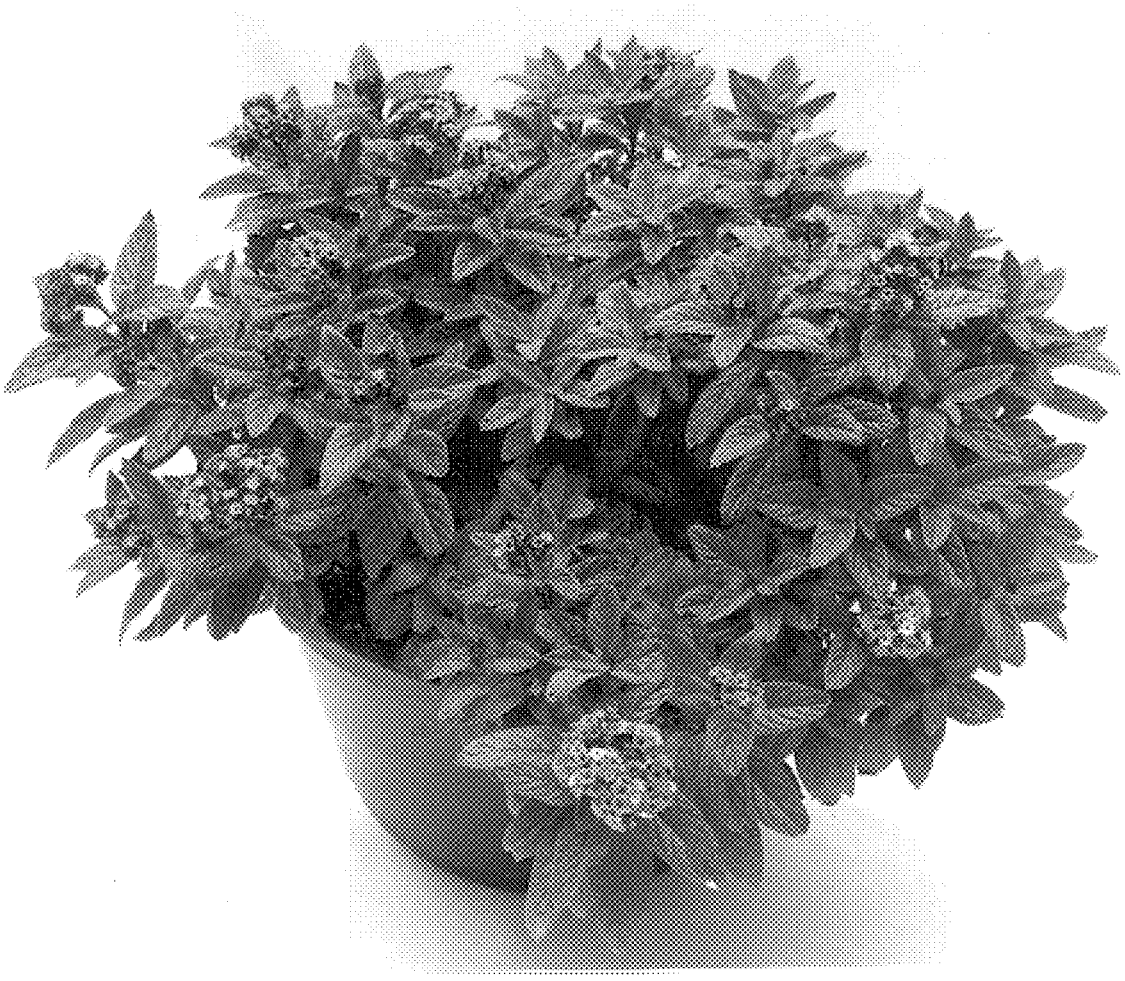

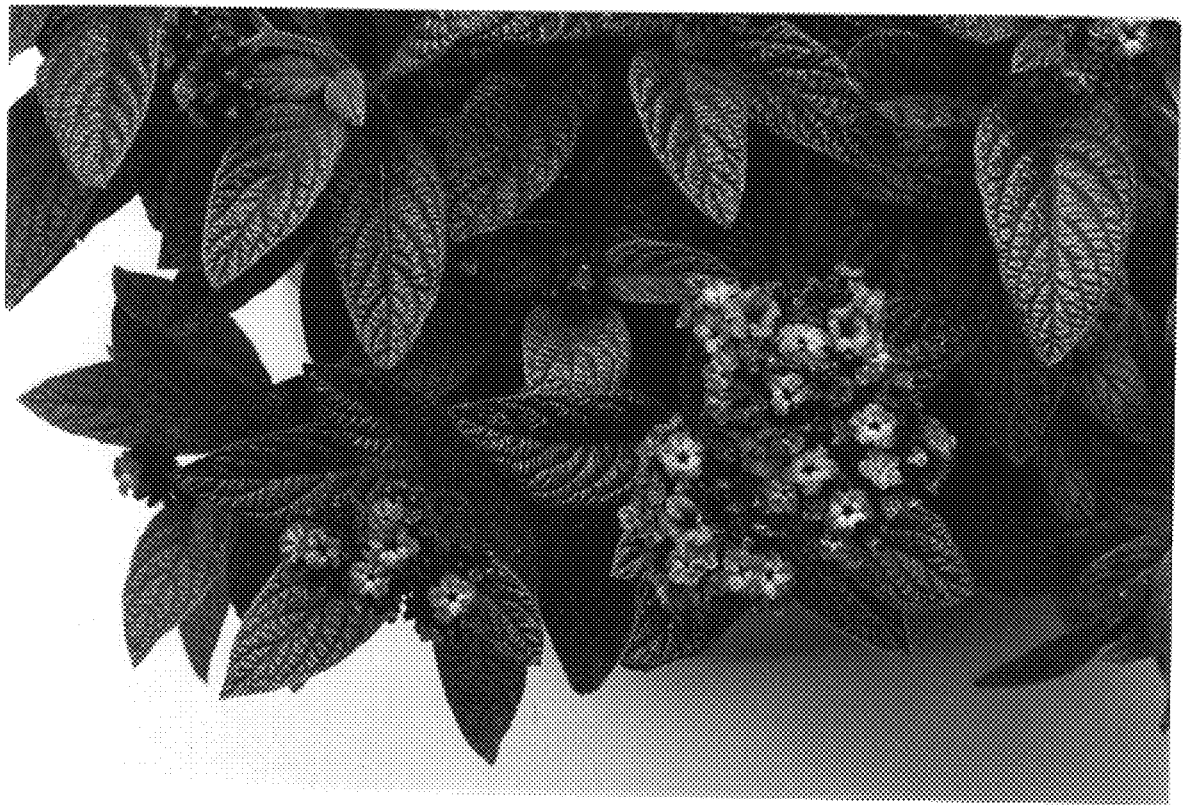
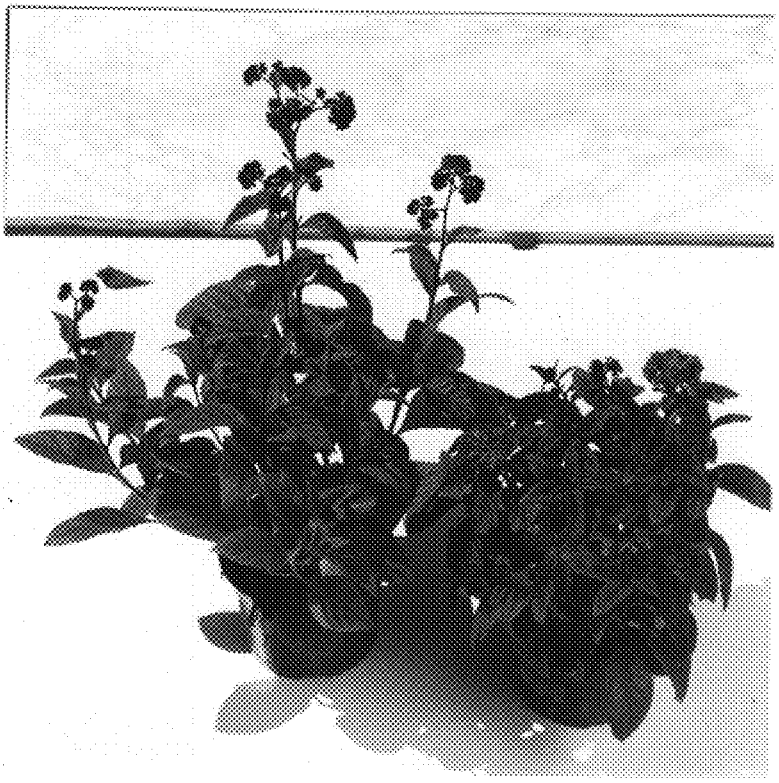

* * * * *